(12) United States Patent
Manning

(10) Patent No.: US 10,983,038 B2
(45) Date of Patent: Apr. 20, 2021

(54) APPLYING TRIAXIAL STRESSES TO A CORE SAMPLE DURING PERFORATION AND FLOW TESTING

(71) Applicant: HALLIBURTON ENERGY SERVICES, INC., Houston, TX (US)

(72) Inventor: John Douglas Manning, Alvarado, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 0 days.

(21) Appl. No.: 15/763,788

(22) PCT Filed: Oct. 4, 2017

(86) PCT No.: PCT/US2017/055134
§ 371 (c)(1),
(2) Date: Mar. 27, 2018

(87) PCT Pub. No.: WO2019/070252
PCT Pub. Date: Apr. 11, 2019

(65) Prior Publication Data
US 2020/0225137 A1 Jul. 16, 2020

(51) Int. Cl.
*G01N 11/00* (2006.01)
*E21B 49/02* (2006.01)
(Continued)

(52) U.S. Cl.
CPC .............. *G01N 11/00* (2013.01); *E21B 43/11* (2013.01); *E21B 49/02* (2013.01); *E21B 49/08* (2013.01);
(Continued)

(58) Field of Classification Search
CPC . G01N 11/00; G01N 3/12; G01N 3/08; G01N 3/10; G01N 33/24;
(Continued)

(56) References Cited

U.S. PATENT DOCUMENTS 3,728,895 A 4/1973 Shaw
5,159,828 A * 11/1992 Steiger .................. E21B 49/006
73/38
(Continued)

FOREIGN PATENT DOCUMENTS

CN 105938070 A 9/2016
CN 106053231 A * 10/2016

OTHER PUBLICATIONS

International Search Report and Written Opinion; PCT Application No. PCT/US2017/055134; dated Oct. 4, 2017.
(Continued)

*Primary Examiner* — Ryan D Walsh
(74) *Attorney, Agent, or Firm* — Polsinelli PC

(57) ABSTRACT

Apparatuses and methods for applying triaxial stresses to a core sample during perforation and flow testing. A core sample of rock is positioned within a fixture shell of an overburden stress apparatus, which is placed within a pressure vessel. The pressure vessel applies a vessel pressure to the overburden stress apparatus. The overburden stress apparatus contains a plurality of stress members which apply overburden stresses to the core sample along its three principal axes. The applied overburden stresses are resisted by a combination of the structural integrity of the overburden stress apparatus and the circumferential support applied to the overburden stress apparatus by the vessel pressure. With the overburden stresses applied, the core sample can undergo perforation testing, production testing, and injection testing.

19 Claims, 5 Drawing Sheets

(51) Int. Cl.
- *G01N 3/10* (2006.01)
- *G01N 33/24* (2006.01)
- *E21B 43/11* (2006.01)
- *E21B 49/08* (2006.01)
- *G01N 3/12* (2006.01)
- *G01N 3/08* (2006.01)

(52) U.S. Cl.
CPC .............. *G01N 3/08* (2013.01); *G01N 3/10* (2013.01); *G01N 3/12* (2013.01); *G01N 33/24* (2013.01); *G01N 2203/0019* (2013.01); *G01N 2203/0042* (2013.01); *G01N 2203/0256* (2013.01)

(58) Field of Classification Search
CPC ... G01N 2203/0019; G01N 2203/0042; G01N 2203/0256; E21B 43/11; E21B 49/08; E21B 49/02
See application file for complete search history.

(56) References Cited

U.S. PATENT DOCUMENTS

| | | | |
|---|---|---|---|
| 5,178,005 A * | 1/1993 | Peterson | G01N 29/07 73/152.11 |
| 7,536,921 B1 | 5/2009 | Chu et al. | |
| 10,564,079 B2 * | 2/2020 | Ma | G01N 33/24 |
| 2005/0150273 A1 * | 7/2005 | Potter | G01N 3/10 73/38 |
| 2009/0241700 A1 * | 10/2009 | Haggerty | G01N 33/24 73/865.6 |
| 2011/0271751 A1 * | 11/2011 | Brooks | G01V 11/002 73/152.07 |
| 2013/0312510 A1 * | 11/2013 | Brooks | E21B 43/11 73/152.01 |
| 2014/0122035 A1 | 5/2014 | Dean | |
| 2014/0137660 A1 | 5/2014 | Meadows | |
| 2015/0111716 A1 * | 4/2015 | Hakimuddin | G01N 33/241 494/10 |
| 2017/0131192 A1 | 5/2017 | Perez | |
| 2018/0335374 A1 * | 11/2018 | Kanj | E21B 49/006 |
| 2019/0011422 A1 * | 1/2019 | McGregor | E21B 43/11 |

OTHER PUBLICATIONS

Bellarby, Jonathan; "Well Completion Design", pp. 51-52; 2009.
French Search Report and Written Opinion; Application No. 1859418; dated Sep. 29, 2020.
English abstract of CN105938070; retrieved from www.epacenet.com dated Feb. 19, 2021.

* cited by examiner

APPLYING TRIAXIAL STRESSES TO A CORE SAMPLE DURING PERFORATION AND FLOW TESTING

TECHNICAL FIELD

The present technology pertains to perforation and flow testing of core samples of rock, and more specifically to applying triaxial overburden stresses to simulate real-world downhole conditions during the testing.

BACKGROUND

Many oil and gas wells today are commonly completed via a process of casing and perforation, in which portions of a borehole are lined with a pipe or casing. Often, the outer surface of the casing is cemented into place, thereby affixing the casing to the borehole. While casing can provide reinforcement and stability, it must additionally be perforated in order to flow production fluid from a formation. As such, the final stage of such a completion will involve running one or more perforating guns down to the desired borehole depth and firing the perforating guns to perforate the casing. While perforating guns employ shaped charges that can be tailored to fit predicted downhole conditions and parameters, perforation operations nevertheless remain an inexact process.

The American Petroleum Institute (API), in its Recommended Practice for Evaluation of Well Perforators (API RP 19B, Sections 2 and 4) has provided a basis for the evaluation of perforators and perforating guns through the use of tests using rock cores at simplified insitu conditions. The primary useful data output from these tests is the penetration depth produced as a function of the target composition and state. In a standard API RP 19B Section 2 or Section 4 test, a cylinder of rock (also referred to as a "core") is jacketed in a rubber sleeve and stressed to simulate various subsurface stresses present in an oil or gas reservoir. This stress is applied by placing the jacketed core in a pressure vessel, which is then pressurized against the jacketed core. With these stresses present, one or more perforation operations are performed and measured.

However, the core isostatically or hydrostatically stressed, meaning that the applied stress is uniform in all directions around the core. However, in reality, the subsurface stress state is not uniform. For example, in the traditional 3-dimensional Cartesian coordinate system, three principal stresses act along the X, Y, and Z axes, with each principal stress having its own magnitude. As such, it would be desirable to provide a triaxial stress test, or a test that is capable of applying three distinct stresses to a rock sample, for use in perforation and flow evaluation operations.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Figure 1A:
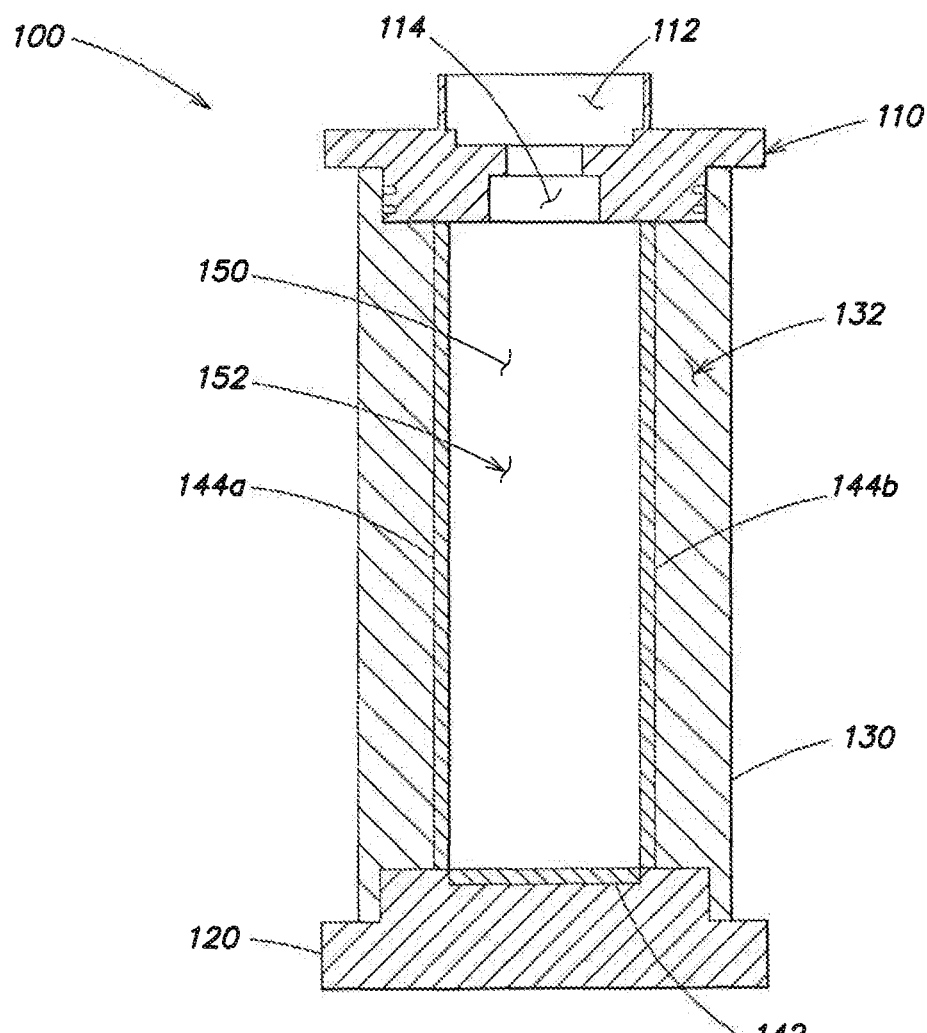
FIG. 1A illustrates a front cross-sectional view of an example triaxial stress apparatus of the present disclosure.

Various embodiments of the disclosure are discussed in detail below. While specific implementations are discussed, it should be understood that this is done for illustration purposes only. A person skilled in the relevant art will recognize that other components and configurations may be used without departing from the spirit and scope of the disclosure.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

Unless otherwise specified, any use of any form of the terms "connect," "engage," "couple," "attach," or any other term describing an interaction between elements is not meant to limit the interaction to direct interaction between the elements and also may include indirect interaction between the elements described. In the following discussion and in the claims, the terms "including" and "comprising" are used in an open-ended fashion, and thus should be interpreted to mean "including, but not limited to . . . ". Reference to up or down will be made for purposes of description with "up," "upper," "upward," "upstream," or "uphole" meaning toward the surface of the wellbore and with "down," "lower," "downward," "downstream," or "downhole" meaning toward the terminal end of the well, regardless of the wellbore orientation. The various characteristics described in more detail below, will be readily apparent to those skilled in the art with the aid of this disclosure upon reading the following detailed description, and by referring to the accompanying drawings.

The approaches set forth herein describe an apparatus and method for performing a triaxial stress test on a rock or core sample in order to simulate the subsurface stresses of an oil or gas reservoir. In particular, the stress test can be performed in accordance with various aspects of Section 2 and Section 4 of API RP 19B, the American Petroleum Institute's Recommended Practice for the Evaluation of Well Perforators. The apparatus comprises an elongate fixture shell containing a chamber adapted to be loaded with a core sample of rock to be tested, and a first end and second end adapter to receive respective first and second ends of the core sample and seal the core sample within the chamber of the fixture shell. A coupling element couples the apparatus within the interior volume of an external pressure vessel, at which point a plurality of stress members within a chamber of the fixture shell apply overburden pressures (and therefore overburden stress profiles) along the three principal axes (e.g. x, y, and z, in Cartesian coordinates) of the core sample. Because the external pressure vessel is pressurized to a vessel pressure, the fixture shell is circumferentially supported by the vessel pressure. Therefore the fixture shell can be sized to only structurally withstand a portion of the vessel pressure or a portion of each of the overburden pressures, whichever is largest. The method comprises loading a core sample of rock within a fixture shell of an overburden stress apparatus and positioning the apparatus within the interior volume of an external pressure vessel. The pressure vessel is then pressurized to a desired vessel pressure, such that the vessel pressure provides circumferential support to the fixture shell, and the overburden stress apparatus is pressurized to desired overburden pressures along the three principal axes (e.g. x, y, and z in Cartesian coordinates) of the core sample.

Figure 1C:
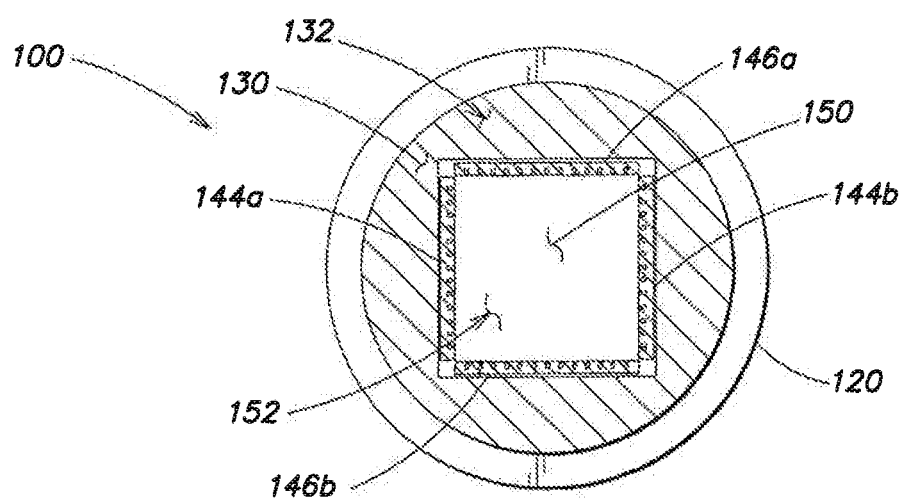
FIG. 1C illustrates a top-down cross-sectional view of an example triaxial stress apparatus of the present disclosure.
Figure 1B:
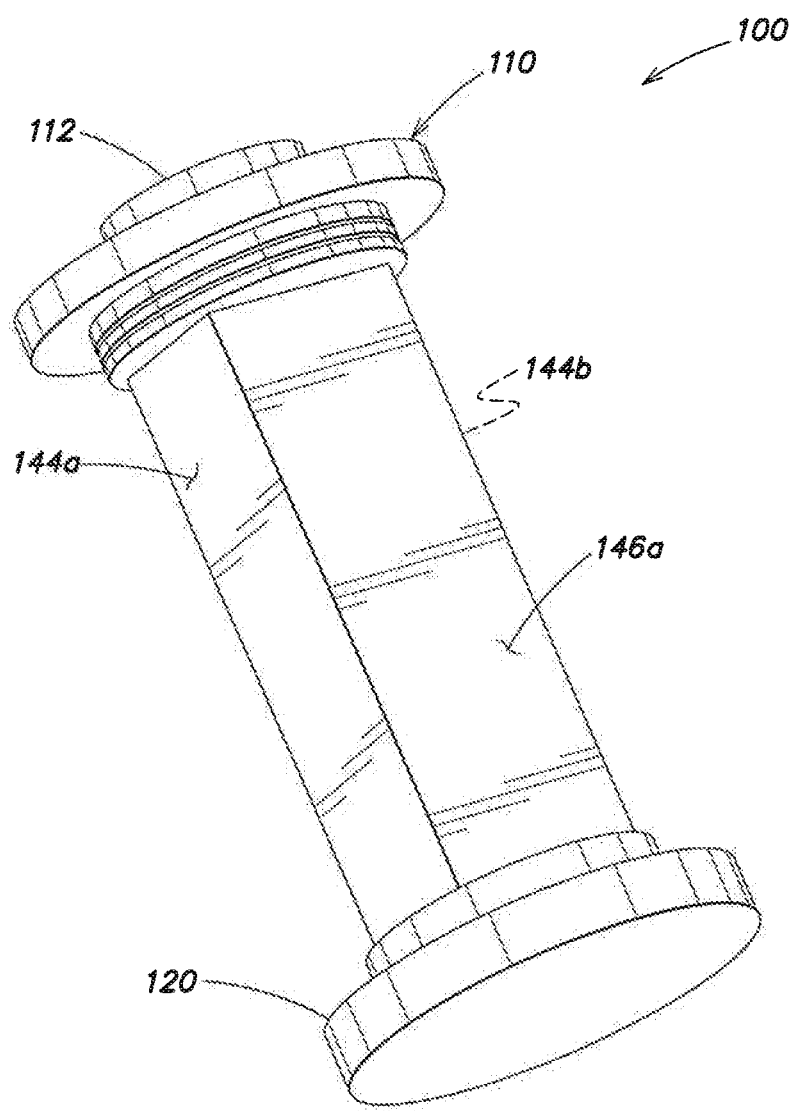
FIG. 1B illustrates a perspective view of an example triaxial stress apparatus of the present disclosure.

Turning now to FIGS. 1A-C, an example triaxial stress apparatus 100 (also referred to herein as a 'test apparatus') of the present disclosure is shown from various perspectives. FIG. 1A illustrates a front cross-sectional view of the test apparatus 100, FIG. 1B illustrates a perspective view of the test apparatus 100, and FIG. 1C illustrates a top-down cross-sectional view of the test apparatus 100. Generally speaking, test apparatus 100 is provided to both contain a core sample 150 and couple to a pressure vessel (not shown) to perform one or more tests of the present disclosure. As seen in FIG. 1A, test apparatus 100 is provided with an upper adapter 110 (alternatively referred to herein as a 'first end adapter') for purposes of coupling to a pressure vessel. An example of such a coupling can be seen in FIG. 2, which shows test apparatus 100 coupled to pressure vessel 205.

Returning to FIG. 1A, upper adapter 110 additionally comprises a perforating port 112, which is adapted to receive a perforator or perforating gun for performing a perforation test on core sample 150. Additionally, a simulated casing and cement coupon can be placed within a casing receptacle 114 such that the simulated casing and cement coupon abuts the face of core sample 150. An empty space formed between perforating port 112 and casing receptacle 114 is referred to as a fluid gap. The thickness of the fluid gap, casing, and cement layers are each adjusted in order to simulate the specific well being tested, wherein the thickness of each layer is determined by one or more of borehole diameter, casing diameter and weight, and perforating gun system diameter.

While traditional API RP 19B Section 2 and Section 4 tests make use of a cylindrical core sample, the present apparatus and method are configured to employ a cubical core sample, which can be square or rectangular in its cross-section. Such cubical core samples are more readily subjected to triaxial stresses, whereas cylindrical core samples are not. Accordingly, while core sample 150 is depicted as having a square cross section, it is understood that various other core sample geometries may be employed without departing from the scope of the present disclosure. In some embodiments, core sample 150 might be dimensioned to be 7"×7"×24" (L×W×H), offering a far smaller and more economical alternative to existing triaxial stress tests that require large blocks of rock that are at least 3 feet or greater on edge.

Because core sample 150 is cubical, it has six external faces—a top face, a bottom face, and four lateral or side faces. As mentioned previously, the top face abuts perforating port 114. The five remaining faces are each in contact with a stress member for applying the desired stress profile to core sample 150. FIG. 1A depicts x-axis stress members 144a and 144b, which apply stress along the x-axis, and z-axis stress member 142, which applies stress along the z-axis. FIG. 1B additionally depicts y-axis stress member 146a, which applies stress along the y-axis, with a second y-axis stress member 146b not visible. FIG. 1C depicts both x-axis stress members 144a and 144b, and both y-axis stress members 146a and 146b.

In conjunction, these five stress members can be operated to apply a triaxial stress profile to core sample 150, as is desired. Due to their contact arrangement with a corresponding five faces of the core sample 150, the five stress members are arranged to form a rectangular prism shaped central receiving cavity 152 for containing the core sample 150. As illustrated, only the upper end (near upper adapter 110) of this central receiving cavity 152 is not covered by a stress member.

In some embodiments, one or more of the stress members 142, 144a, 144b, 146a, 146b, can be provided as flat jacks, which are inflated in order to apply the desired stress. However, flat jacks can experience variations in the stress applied in response to a given inflation input, or otherwise have varying pressure responses, and as such can require calibration and adjustment before a test can be performed. As such, in some embodiments, one or more of the stress members 142, 144a, 144b, 146a, 146b, can be provided as pistons, although it is understood that various other stress members beyond flat jacks and pistons can be employed, so long as the desired pressure and stress response is elicited.

As illustrated, the stress members are contained within a chamber 132 of an elongate fixture shell 130, which may also act to partially or fully support one or more of the stress members. In some embodiments, shell 130 can be designed such that is unique to the dimensions of a given core sample 150 and the associated stress members. For example, shell 130 could be a solid machined piece of metal or other unitary construction. In some embodiments, shell 130 can comprise two or more pieces, as a multi-piece construction can increase machinability and modularity while reducing costs. In some embodiments, shell 130 can be designed such that its interior chamber 132 is compatible with core samples of varying dimensions and stress members of varying type or dimensions. Regardless of whether shell 130 is adjustable or not, it functions to contain core sample 150 and its associated stress members, such that both the core sample and stress members are fluidly isolated from the pressure vessel into which test apparatus 100 is ultimately placed. Additionally, shell 130 is designed such that it is able to support and withstand the stresses that are applied by the various stress members, as well as the stresses that are applied by an external pressure vessel into which test apparatus 100 is placed.

Additionally, shell 130 is designed to contain control lines, such as hydraulic and electrical lines, that can be used to control or otherwise adjust the stress that is applied by the various stress members. Further still, while not shown, shell 130 can be designed to incorporate various pressure, flow, temperature, and other sensors utilized in accordance with making obtaining relevant data used in conducting perforation and flow tests such as those described in API RP 19B Sections 2 and 4. In some embodiments, shell 130 can be utilized to couple upper adapter 110 to lower adapter 120. In some embodiments, all-thread or various other connecting methods and apparatus known in the art can be used to couple upper adapter 110 to lower adapter 120, either in conjunction with or absent any support that may be provided by shell 130.

As illustrated, lower adapter 120 contains and supports the z-axis stress member 142. Like shell 130, lower adapter 120 is designed to withstand both the stresses applied by z-axis stress member 142 and the stresses that are applied by the external pressure vessel into which test apparatus 100 is placed. In some embodiments, lower adapter 120 can additionally contain a receiving mechanism for grasping and centering core sample 150 within test apparatus 100. Such a centered arrangement can be seen in the top-down cross section presented by FIG. 1C. Lower adapter 120 can additionally be configured to provide a fluid connection to a source of pore fluid, which is used to simulate a reservoir fluid that is flowed after the perforation event of the test. The pore fluid can be introduced at or along the bottom face of the core sample 150, and allowed to permeate or otherwise penetrate core sample 150. In some embodiments, this source of pore fluid is configured to match the composition and pressure of a real-life borehole that is the subject of the perforation or flow test at hand. In some embodiments, the fluid connection of lower adapter 120 can be provided as a flow distributor, which can distribute pore fluids that are in liquid or gaseous form. Although not illustrated, additional fluid couplings can be provided to distribute pore fluid to other faces of core sample 150 and induce fluid flow in different directions. For example, fluid couplings can be provided to allow bi-directional axial flow, that is, bottom-to-top or top-to-bottom with respect to upper adapter 110 and lower adapter 120. Fluid couplings can also be provided to allow radial flow, such that fluid flows into the core and out through a perforation created during a perforation test. Additionally, it is contemplated that fluid flow configurations can consists of any combination of the axial and radial flows described above, and furthermore, that the directionality of fluid flow can be reversible, including while under test.

Figure 2:
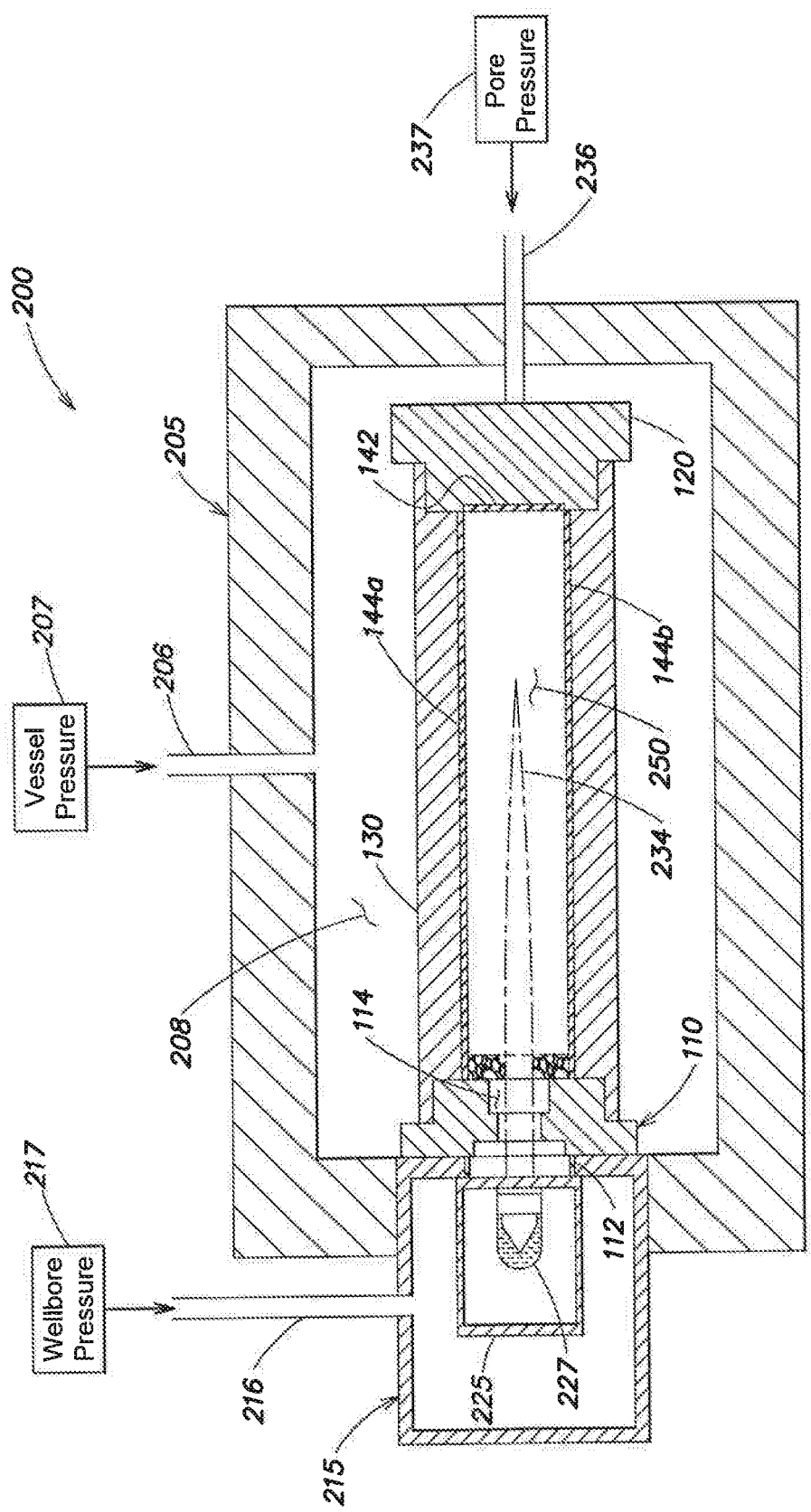
FIG. 2 illustrates a first side cross-sectional view of an example test system employing the triaxial stress apparatus of the present disclosure.

With the above description of test apparatus 100 in mind, the disclosure turns now to FIG. 2, which presents a cross-sectional diagram of an exemplar system 200 of the present disclosure. Generally, system 200 consists of the arrangement of test apparatus 100 within an external pressure vessel 205, with various coupled pressure sources. It is contemplated that such a system and arrangement would be employed to conduct one or more of the various tests considered by the present disclosure.

In some embodiments, external pressure vessel 205 is water-based, meaning that that interior volume 208 of external pressure vessel 205 is filled with water, which is then pressurized to a desired pressure, although the interior volume 208 of external pressure vessel 205 may also be filled with various other media as desired, such as Odorless Mineral Spirits (OMS). External pressure vessel 205 may itself contain pressurization apparatus, or may be connected to a pressure source. As illustrated, pressure vessel 205 is coupled to a source of vessel pressure 207 via a conduit 206. This vessel pressure is applied relatively uniformly along the exterior surface of test apparatus 100, i.e. along the exterior surface of shell 130, upper adapter 110, and lower adapter 120. The vessel pressure can be selectable among various levels, and in some embodiments might have a ceiling of 25 ksi (i.e. 25,000 psi), although other pressure ceilings may be employed as desired. Additionally, it is further understood that various other pressure vessels and pressure vessel fluids may likewise be employed without departing from the scope of the present disclosure. As mentioned previously, once test apparatus 100 is placed within the interior volume 208 of external pressure vessel 205, the shell 130 of the test apparatus serves to fluidly isolate test apparatus 100 from any pressure vessel fluid.

Pressure vessel 205 additionally comprises a wellbore test chamber 215 which is used to simulate conditions inside the wellbore or borehole itself. A source of wellbore pressure 217 is coupled to wellbore test chamber 215 via a wellbore conduit 216, and is adjustable to provide a wellbore pressure within the wellbore test chamber 215 as is desired.

In order to prepare for and perform a perforating test, test apparatus 100 is coupled to external pressure vessel 205 via upper adapter 110. A desired cement and casing coupon can be installed within the casing receptacle 114 during the assembly and preparation of test apparatus 100. Upper adapter 110 is then connected to wellbore test chamber 215, at which point in time the two coupled components are placed inside pressure vessel 205. A perforating test assembly 225, such as a lab perforating gun, contains a perforating charge 227 and is placed within or otherwise coupled to perforating port 112. The perforating charge 227 may be shaped or adjusted in accordance with the desired perforation characteristics or parameters that are associated with the perforation test to be conducted with test apparatus 100.

With perforating charge 227 in place, wellbore test chamber 215 is filled with a wellbore fluid specific to the perforating test being conducted and is capped or sealed. At this point, external pressure vessel 205 is subjected to an initial pressure from the source of vessel pressure 207. Subsequently, an initial pore pressure is applied from a source of pore pressure 237, and an initial wellbore pressure is applied to wellbore test chamber 215 from source of wellbore pressure 217. The vessel pressure can be transmitted by the pressure vessel fluid, the pore pressure can be transmitted by a pore fluid, and the wellbore pressure can be transmitted by a wellbore fluid. It is also noted that these initial pressure values are all typically far lower than the final desired pressure values.

With these initial pressures in place, one or more of the stress members 142, 144a, 144b, 146a, 146c are actuated to apply initial tri-axial stresses to core sample 215, e.g. along the X, Y, and Z-axes. With all initial pressures and initial triaxial stresses applied, the pressures and stresses are slowly stepped up together until the desired test conditions have been achieved.

After test conditions have been achieved, perforating charge 227 can be detonated, which causes the charge to penetrate the scallop of the perforating gun, the casing and cement layers within casing receptacle 114, and finally the core 250 itself. At this point, with a perforation 234 created, flow testing can be initialized in either a production configuration (fluid flows out of the perforation) or an injection configuration (fluid flows into the perforation).

Further details and aspects of the use of test apparatus 100 to perform a perforation test are discussed below. During either setup, testing, or both, lower adapter 120 may be free floating in the interior volume 208 of external pressure vessel 205 such that test apparatus 100 is cantilevered from the connection point provided at upper adapter 110. In some embodiments, lower adapter 120 might be supported or otherwise attached to pressure vessel 205 such that test apparatus 100 is not cantilevered. As mentioned previously, lower adapter 120 can contain a fluid distributor, which can distribute pore fluid from the source of pore pressure 237 in order to transmit a desired pore pressure. In some embodiments, the conduit 236 for providing this coupling may further be utilized to support the lower adapter end of test apparatus 100.

Conduit 236 and the source of pore pressure 237 may both be located outside of pressure vessel 205, in which case the pressure vessel 205 can be sealed to ensure there is no leakage from its interior volume 208 at an entry port of conduit 236. As mentioned previously, casing receptacle 114 may be loaded with any casing and cement layers that are needed to simulate the real-world wellbore and surrounding formation that are the subject of the test. However, in some embodiments, more than one casing string may be needed to simulate the well of interest. In such a scenario, receptacle 114 could be used to receive a simulated inner tubing and annulus (not shown), while the casing and cement coupon could be relocated to the face of core sample 250. In this manner, both the inner tubing and annulus are simulated along with an outer casing and cement, lending additional flexibility to the disclosed test apparatus and method.

Once test apparatus 100 has been loaded, it can be placed within the interior volume 208 of the pressure vessel 205 and coupled to the pressure vessel 205 via upper adapter 110. Lower adapter 120 of the test apparatus can also be coupled to conduit 236, although the source of pore pressure 237 preferably remains disconnected or off during this initial process of loading test apparatus 100 into the pressure vessel 205. Likewise, the source of wellbore pressure 217 preferably remains disconnected or off during this initial loading process.

At this point in time, the test apparatus 100 and external pressure vessel 205 should be suitably configured and ready to begin a pressurization ramp up to the desired levels for the perforation test. The pressurization process begins by first sealing test apparatus 100 within the interior volume 208 of pressure vessel 205. While pressure vessel 205 may ultimately be pressurized to a vessel pressure such as 25 ksi, such a pressurization is performed gradually, in a step-wise manner with adjustments being made in turn to the vessel pressure and then to one or more of the stress members 142, 144a, 144b, 146a, 146c.

Recalling that the vessel pressure generally acts on the test apparatus in a uniform manner, it is seen that conventional approaches to perforation testing which utilize the vessel pressure itself to simulate a formation overburden pressure are thus not capable of applying triaxial stresses to a core sample.

However, in the presently disclosed approach, the vessel pressure is not used to simulate the formation overburden pressure. Instead, the overburden pressures, or more specifically, the resulting overburden stresses acting on core sample 250, are simulated by the stress members 142, 144a, 144b, 146a, 146b. For example, z-axis stress member 142 could apply an overburden pressure of 20 ksi along the z-axis, x-axis stress members 144a and 144b could apply an overburden pressure of 19 ksi along the x-axis, and y-axis stress members 146a and 146b could apply an overburden pressure of 17 ksi along the y-axis. It is understood that these numbers are provided solely by way of example, and that in practice, the overburden pressures and overburden stress profiles developed by the stress members 142, 144a, 144b, 146a, 146b can be adjusted to replicate the actual three-axis overburden stress profile that would be experienced in the wellbore and formation being simulated for the perforation test.

In this sense, the vessel pressure is not relied upon to generate the formation overburden pressure, and therefore is not relied upon to generate the overburden stress within the core sample 250. However, the vessel pressure is advantageously employed to support the test apparatus 100, and to thereby reduce the strength requirements of one or more of shell 130, upper adapter 110, and lower adapter 120. Because the pressurized fluid of the pressure vessel 205 acts to support the test apparatus 100, test apparatus 100 must only support the difference in pressure between the vessel pressure and the overburden pressure applied by the stress members.

Figure 3:
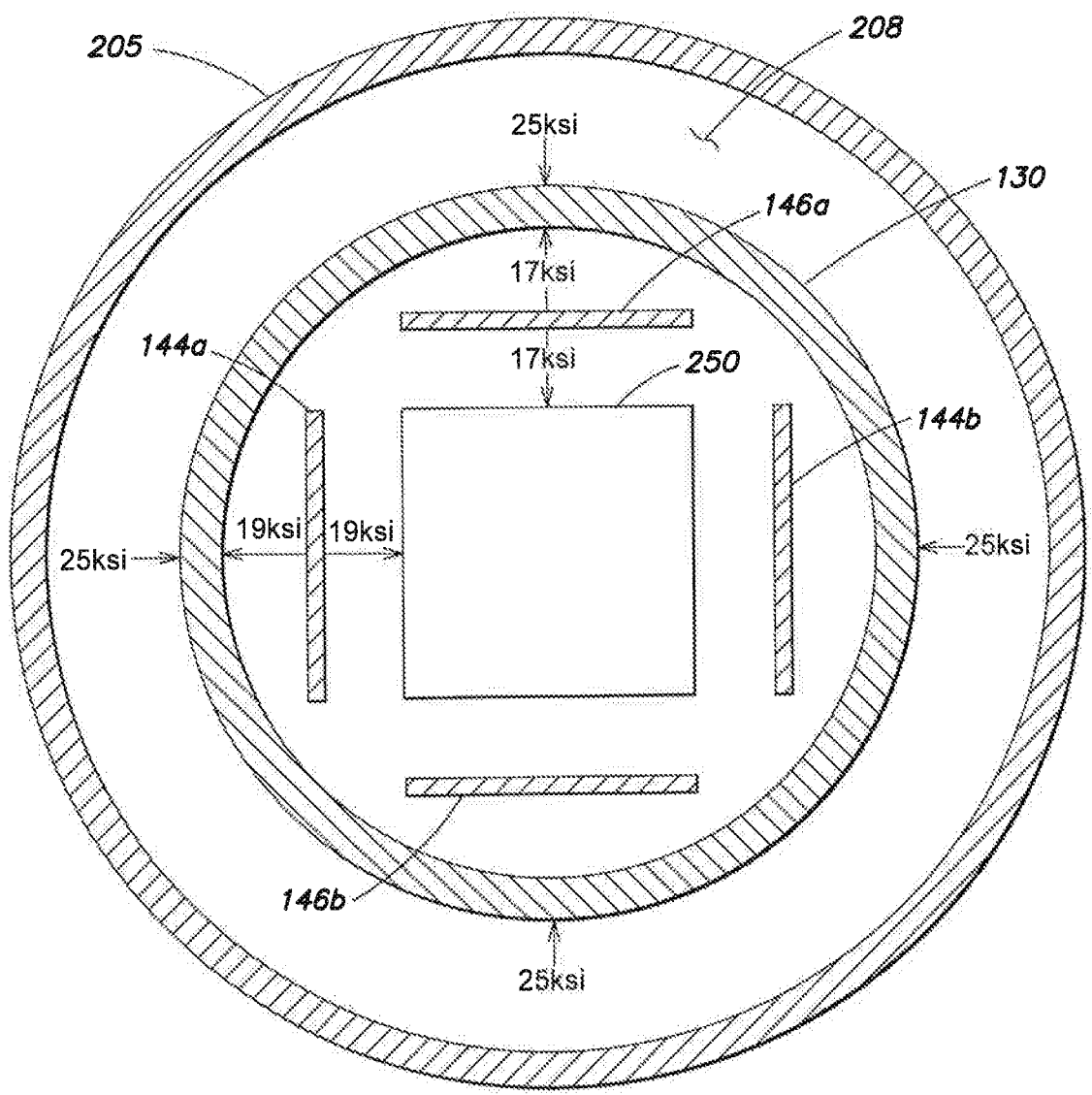
FIG. 3 illustrates a second side cross-sectional view of the example test system of FIG. 2, annotated to indicate example pressure differentials in the system.

An example of this support provided by the vessel fluid is illustrated in FIG. 3, which illustrates a cut-away view of the system of FIG. 2. Note that for the purposes of illustration, the stress members 144a, 144b, 146a, 146b, are shown in simplified form and not in contact with core sample 250, although such contact is generally utilized in order to apply the overburden pressures and overburden stress profiles. In this example, pressure vessel 205 is pressurized to a vessel pressure of 25 ksi, which acts uniformly along the exterior surface of shell 130 of test apparatus 100. The x-axis stress member 144a applies an overburden pressure of 19 ksi to the core sample 250 along the x-axis. This generates a reaction pressure of 19 ksi acting on the interior of shell 130, also along the x-axis. In an approach utilizing only the stress members and no external pressure vessel 205, shell 130 would be required to support a pressure of at least 19 ksi along the x-axis. However, in the presently disclosed approach utilizing both the stress members and the external pressure vessel 205, shell 130 is instead only required to support the difference between the vessel pressure and the overburden pressure generated by the stress members. In this case, shell 130 would be required to support a pressure of at least 6 ksi along the x-axis, instead of 19 ksi.

The same principle applies to the remaining stress members. As shown, y-axis stress member 146a applies an overburden pressure of 17 ksi to the core sample 250 along the y-axis, which leads to a reaction pressure of 17 ksi acting on the interior of shell 130, also along the y-axis. Once again, shell 130 is only required to support the difference between the overburden pressure and the vessel pressure, meaning that in this case shell 130 would be required to support a pressure of at least 8 ksi along the y-axis, instead of 17 ksi. Similarly, if z-axis stress member 142 applies an overburden pressure of 20 ksi, shell 130 is only required to support a pressure of at least 5 ksi along the z-axis, instead of 20 ksi.

As such, the engineering requirements of the shell 130, and test apparatus 100 in general, are greatly reduced by the use of pressure vessel 205 and its pressurized fluid to assist in providing resistance to the overburden pressures being applied by the stress members 142, 144a, 144b, 146a, 146b. Advantageously, shell 130, upper adapter 110, and lower adapter 120 can all be made much thinner, lighter, and smaller than would otherwise be required to support the full overburden pressures and overburden stresses that are applied by the various stress members. This reduces both capital and operational costs associated with performing such testing, and reduces the overall size of test apparatus 100 and the core sample 250, as compared to conventional triaxial stress frame testing, which is quite cumbersome and expensive to perform. Further still, the combined system of test apparatus 100 and external pressure vessel 205 can achieve higher applied triaxial overburden stresses than those that can be achieved by the conventional triaxial stress frame testing, in a further advantage of the present disclosure.

In light of the discussion above, in which shell 130 is required to support at least 6 ksi along the x-axis, 8 ksi along the y-axis, and 5 ksi along the z-axis, it is apparent why the pressurization process of the overall system of FIG. 2 must proceed in a step-wise or synchronous fashion. Assuming that the shell 130 is designed with a safety margin in mind and can support 12 ksi in all directions, a failure would nevertheless occur if pressure vessel 205 were brought to a relative pressure of 25 ksi against the test apparatus 100 at ambient pressure—the resulting pressure differential of 25 ksi would far surpass shell 130's design limit of 12 ksi.

Instead, the pressure vessel 205 and the test apparatus 100 should be brought up to pressure together, such that the pressure limit of the test apparatus is never surpassed. Such a pressurization process might consist of pressure vessel 205 being slowly pressurized to 25 ksi while test apparatus 100 is simultaneously brought up to overburden pressures of 19 ksi, 17 ksi, and 20 ksi along the x, y, and z axes respectively, using the stress members. In some embodiments, pressure adjustments might be made in a step-wise fashion, wherein the size of a step may be a function of the overall pressure limit of test apparatus 100. For example, with a step size of ¼ of the overall pressure limit, or 3 ksi in the present example, the pressure vessel 205 might first be pressurized to 3 ksi above ambient, at which point test apparatus 100 is supporting 3 ksi. Next, test apparatus 100 might be pressurized to 3 ksi in each direction, such that there is no net pressure acting on it. Alternatively, test apparatus 100 might be pressurized to 6 ksi in each direction, such that there is a net pressure of 3 ksi acting on it. The alternating pressurization of pressure vessel 205 and the stress members of test apparatus 100 can proceed in either such fashion until the final desired pressurizations are achieved.

In some embodiments, the vessel pressure of the external pressure vessel 205, along with the overburden pressures applied by the stress members 142, 144a, 144b, 146a, 146b can be continuously monitored and adjusted such that the desired overburden stress profile is maintained throughout the core sample 250, and such that the pressure limit of test apparatus 100, or some portion thereof, is never exceeded.

Depending on the type of testing to be performed, one or both of the source of wellbore pressure 217 and the source of pore pressure 237 may also be adjusted during the course of setup and testing. For example, the wellbore pressure source 217 can be pressurized to simulate an anticipated wellbore pressure at the depth being simulated—typically the wellbore pressure and the overburden pressure are simulated for the same depth. As another example, in a production test, the pressurized source of pore fluid 237 might be activated to saturate core sample 250 with the pore fluid, either before, during, or after the pressurization of the pressure vessel 205 and the test apparatus 100.

With the final desired pressures thus maintained and achieved, a perforation test can proceed. The perforating charge 227 of perforating assembly 225 (e.g. a perforating gun) is detonated, and creates a hole passing through the scallop of the perforating gun and the casing and cement layers within casing receptacle 114, thereby opening a perforation tunnel 234 that penetrates into the core sample 250. In some embodiments, the core sample 250 might be dimensioned such that at least one core diameter remains below the maximum depth to which the perforation tunnel penetrates. In other words, the minimum height of core sample 250 (where the height is taken between upper adapter 110 and lower adapter 120) might be given by 'maximum anticipated depth of perforation tunnel'+'diameter of core sample'.

In some embodiments, accumulators (not shown) may be plumbed in upstream and downstream of core sample 250 in order to absorb the hydraulic shock of the perforation event and to simulate the pressure surges that accompany a downhole perforation. With perforation tunnel 234 opened up in core sample 250, and with the overburden pressures and stresses still being applied by the stress members 142, 144a, 144b, 146a, 146b, the injection or production from perforation tunnel 234 can be measured. In the case of injection, pressurized fluid would be driven into the perforation tunnel 234 via the source of wellbore pressure 217 in order to simulate a variety of different stimulation and injection operations. The injected fluid flow might be measured and characterized at or near the lower adapter 120 using various embedded sensors contained within test apparatus 100 for the purposes of analyzing fluid flows. In the case of production, pressurized fluid would be driven into the perforation tunnel 234 from the surrounding rock of core sample 250 (i.e. radially), with the motive force provided by the source of pore pressure 237.

In some embodiments, properties and characteristics of perforation tunnel 234 can be inferred from the various telemetry and flow data collected from sensors provided on and within test apparatus 100, such that perforation tunnel 234 is modeled in one or more of its most likely forms. These sensors on or within test apparatus 100 may be utilized in addition to sensors and data collection modules that are provided on or integrated with the pressure vessel 205. In some embodiments, pressure vessel 205 and test apparatus 100 may be de-pressurized, in a similar synchronous or step-wise manner as that in which it was originally pressurized, such that test apparatus 100 may be removed. Upon removal, core sample 250 could be scanned, using, for example, a CT scanner, or could be physically opened such that the perforation tunnel 234 is visible for inspection and analysis.

Figure 4A:
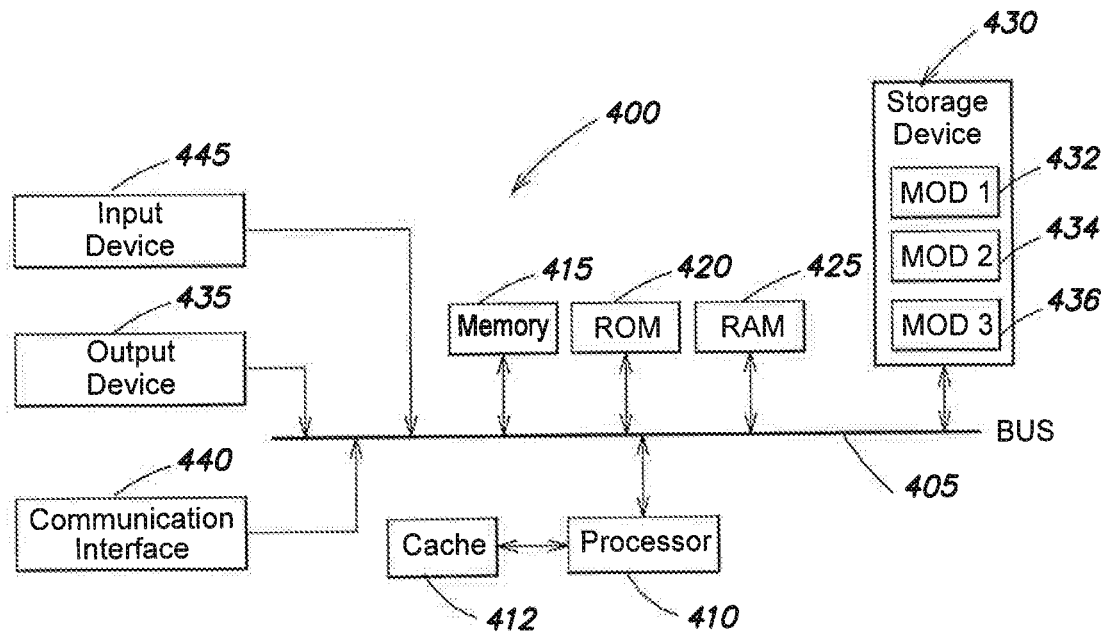
FIGS. 4A and 4B illustrate schematic diagrams of example computing systems for use with example system embodiments.
Figure 4B:
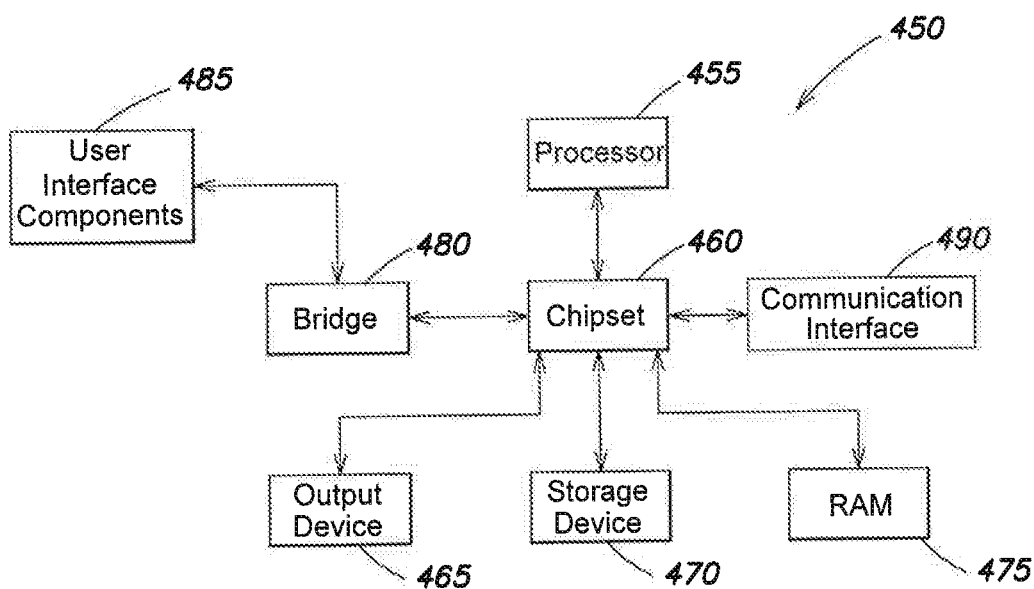

FIG. 4A and FIG. 4B illustrate example computing systems for use as a control device in the example system embodiments. The more appropriate embodiment will be apparent to those of ordinary skill in the art when practicing the present technology. Persons of ordinary skill in the art will also readily appreciate that other system embodiments are possible.

FIG. 4A illustrates a conventional system bus computing system architecture 400 wherein the components of the system are in electrical communication with each other using a bus 405. Exemplary system 400 includes a processing unit (CPU or processor) 410 and a system bus 405 that couples various system components including the system memory 415, such as read only memory (ROM) 420 and random access memory (RAM) 425, to the processor 410. The system 400 can include a cache of high-speed memory connected directly with, in close proximity to, or integrated as part of the processor 410. The system 400 can copy data from the memory 415 and/or the storage device 430 to the cache 412 for quick access by the processor 410. In this way, the cache can provide a performance boost that avoids processor 410 delays while waiting for data. These and other modules can control or be configured to control the processor 410 to perform various actions. Other system memory 415 may be available for use as well. The memory 415 can include multiple different types of memory with different performance characteristics. The processor 410 can include any general purpose processor and a hardware module or software module, such as module 1 432, module 2 434, and module 3 436 stored in storage device 430, configured to control the processor 410 as well as a special-purpose processor where software instructions are incorporated into the actual processor design. The processor 410 may essentially be a completely self-contained computing system, containing multiple cores or processors, a bus, memory controller, cache, etc. A multi-core processor may be symmetric or asymmetric.

To enable user interaction with the computing device 400, an input device 445 can represent any number of input mechanisms, such as a microphone for speech, a touch-sensitive screen for gesture or graphical input, keyboard, mouse, motion input, speech and so forth. An output device 435 can also be one or more of a number of output mechanisms known to those of skill in the art. In some instances, multimodal systems can enable a user to provide multiple types of input to communicate with the computing device 400. The communications interface 440 can generally govern and manage the user input and system output. There is no restriction on operating on any particular hardware arrangement and therefore the basic features here may easily be substituted for improved hardware or firmware arrangements as they are developed.

Storage device 430 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 425, read only memory (ROM) 420, and hybrids thereof.

The storage device 430 can include software modules 432, 434, 436 for controlling the processor 410. Other hardware or software modules are contemplated. The storage device 430 can be connected to the system bus 405. In one aspect, a hardware module that performs a particular function can include the software component stored in a computer-readable medium in connection with the necessary hardware components, such as the processor 410, bus 405, display 435, and so forth, to carry out the function.

FIG. 4B illustrates an example computer system 450 having a chipset architecture that can be used in executing the described method and generating and displaying a graphical user interface (GUI). Computer system 450 is an example of computer hardware, software, and firmware that can be used to implement the disclosed technology. System 450 can include a processor 455, representative of any number of physically and/or logically distinct resources capable of executing software, firmware, and hardware configured to perform identified computations. Processor 455 can communicate with a chipset 460 that can control input to and output from processor 455. In this example, chipset 460 outputs information to output device 465, such as a display, and can read and write information to storage device 470, which can include magnetic media, and solid state media, for example. Chipset 460 can also read data from and write data to RAM 475. A bridge 460 for interfacing with a variety of user interface components 465 can be provided for interfacing with chipset 460. Such user interface components 465 can include a keyboard, a microphone, touch detection and processing circuitry, a pointing device, such as a mouse, and so on. In general, inputs to system 450 can come from any of a variety of sources, machine generated and/or human generated.

Chipset 460 can also interface with one or more communication interfaces 490 that can have different physical interfaces. Such communication interfaces can include interfaces for wired and wireless local area networks, for broadband wireless networks, as well as personal area networks. Some applications of the methods for generating, displaying, and using the GUI disclosed herein can include receiving ordered datasets over the physical interface or be generated by the machine itself by processor 455 analyzing data stored in storage 470 or 475. Further, the machine can receive inputs from a user via user interface components 465 and execute appropriate functions, such as browsing functions by interpreting these inputs using processor 455.

It can be appreciated that example systems 400 and 450 can have more than one processor 410 or be part of a group or cluster of computing devices networked together to provide greater processing capability.

For clarity of explanation, in some instances the present technology may be presented as including individual functional blocks including functional blocks comprising devices, device components, steps or routines in a method embodied in software, or combinations of hardware and software.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the aforementioned description can be implemented using computer-executable instructions that are stored or otherwise available from computer readable media. Such instructions can comprise instructions and data which cause or otherwise configure a general purpose computer, special purpose computer, or special purpose processing device to perform a certain function or group of functions. Portions of computer resources used can be accessible over a network. The computer executable instructions may be binaries, intermediate format instructions such as assembly language, firmware, or source code. Computer-readable media that may be used to store instructions, information used, and/or information created during methods according to the aforementioned description include magnetic or optical disks, flash memory, USB devices provided with non-volatile memory, networked storage devices, and so on.

For clarity of explanation, in some instances the present technology may be presented as including individual functional blocks including functional blocks comprising devices, device components, steps or routines in a method embodied in software, or combinations of hardware and software.

The computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Devices implementing methods according to these disclosures can comprise hardware, firmware and/or software, and can take any of a variety of form factors. Such form factors can include laptops, smart phones, small form factor personal computers, personal digital assistants, rackmount devices, standalone devices, and so on. Functionality described herein also can be embodied in peripherals or add-in cards. Such functionality can also be implemented on a circuit board among different chips or different processes executing in a single device.

The instructions, media for conveying such instructions, computing resources for executing them, and other structures for supporting such computing resources are means for providing the functions described in these disclosures.

Although a variety of information was used to explain aspects within the scope of the appended claims, no limitation of the claims should be implied based on particular features or arrangements, as one of ordinary skill would be able to derive a wide variety of implementations. Further and although some subject matter may have been described in language specific to structural features and/or method steps, it is to be understood that the subject matter defined in the appended claims is not necessarily limited to these described features or acts. Such functionality can be distributed differently or performed in components other than those identified herein. Rather, the described features and steps are disclosed as possible components of systems and methods within the scope of the appended claims. Moreover, claim language reciting "at least one of" a set indicates that one member of the set or multiple members of the set satisfy the claim.

Statements of the Disclosure Include:

Statement 1: An overburden stress apparatus comprising: an elongate fixture shell enclosing and isolating a chamber; a plurality of stress members within the chamber and arranged to form a rectangular prism shaped central receiving cavity for containing a core sample of rock to be tested, the plurality of stress members covering at least five faces of the rectangular shaped receiving cavity, the rectangular prism shaped receiving cavity having three opposite paired faces and having three axes extending one through each of the three opposite paired faces, the plurality of stress members independently controllable to apply overburden pressures to the core sample when the core sample is contained within the central receiving cavity in the direction of each of the three axes; a first end adapter positioned at a first end of the central receiving cavity for receiving a first end of the core sample when contained therein; and a second end adapter positioned at a second end of the central receiving cavity opposite the first end, and covering at least one of the plurality of stress members.

Statement 2: The overburden stress apparatus of Statement 1, wherein the fixture shell is configured to receive an external pressure from an external pressure vessel, the fixture shell configured support only a portion of the overburden pressures and the external pressure supports a remaining portion of the overburden pressures.

Statement 3: The overburden stress apparatus of Statement 1, further comprising an external pressure vessel, the fixture shell being contained within the external pressure vessel and receiving an external pressure from the external pressure vessel, the fixture shell configured to support only a portion of the overburden pressures, the external pressure supporting a remaining portion of the overburden pressures.

Statement 4: The overburden stress apparatus of Statement 1, wherein the plurality of stress members are independently controllable to generate three overburden stress profiles along the corresponding three axes.

Statement 5: The overburden stress apparatus of Statement 1, wherein the plurality of stress members are provided by one or more of flat jacks and pistons.

Statement 6: The overburden stress apparatus of Statement 5, wherein the core sample is rectangular in cross-section and less than 12 inches on a side in cross-section.

Statement 7: The overburden stress apparatus of Statement 1, further comprising a simulated wellbore section, the simulated wellbore section coupled between the first end adapter and a pressurized fluid source for simulating wellbore characteristics.

Statement 8: The overburden stress apparatus of Statement 1, wherein the first end of the core sample is received into a simulated wellbore casing portion of the first end adapter.

Statement 9: The overburden stress apparatus of Statement 1, wherein the second end adapter provides a fluid coupling between a pressurized source of pore fluid and the core sample.

Statement 10: The overburden stress apparatus of Statement 1, further comprising a perforator coupled to the simulated wellbore casing portion of the first end adapter, the perforator operable to create a perforation tunnel through the simulated wellbore casing portion and into the core sample.

Statement 11: A method, comprising: positioning a core sample of rock within a fixture shell of an overburden stress apparatus; positioning the overburden stress apparatus within the interior volume of an external pressure vessel containing a vessel fluid; pressurizing the external pressure vessel to a desired vessel pressure, such that the vessel pressure provides circumferential support to the fixture shell; and pressurizing the overburden stress apparatus to desired triaxial overburden pressures along a first axis, a second axis, and a third axis of the core sample, wherein the fixture shell supports only a portion of the overburden pressures and the vessel pressure supports the remaining portion of the overburden pressures.

Statement 12: The method of Statement 11, wherein a maximum rated pressure of the fixture shell is less than one or more of the vessel pressure and the triaxial overburden pressures.

Statement 13: The method of Statement 11, further comprising adjusting the triaxial overburden pressures to generate a desired first overburden stress profile along the first axis of the core sample, a desired second overburden stress profile along the second axis of the core sample, and a desired third overburden stress profile along the third axis of the core sample.

Statement 14: The method of Statement 11, wherein the external pressure vessel and the overburden stress apparatus are pressurized simultaneously, such that a differential between the vessel pressure and any of the triaxial overburden pressures never exceeds a threshold pressure, wherein the threshold pressure is a function of a maximum rated pressure of the fixture shell.

Statement 15: The method of Statement 11, wherein the external pressure vessel and the overburden stress apparatus are step-wise pressurized, wherein the vessel pressure and the triaxial overburden pressures are raised in alternating fashion by an amount less than the desired vessel pressure and the desired triaxial overburden pressures, respectively.

Statement 16: The method of Statement 11, wherein pressurizing the overburden stress apparatus comprises adjusting a plurality of stress members positioned in the interior of the fixture shell and in contact with the core sample, the stress members provided by one or more of flat jacks and pistons.

Statement 17: The method of Statement 11, further comprising providing a simulated wellbore casing portion between a face of the core sample and the external pressure vessel.

Statement 18: The method of Statement 17, further comprising performing a perforation test on the core sample, the perforation test creating a perforation tunnel through the simulated wellbore casing portion and extending into the core sample.

Statement 19: The method of Statement 17, wherein the perforation tunnel is used to perform a production test or an injection test on the core sample.

Statement 20: The method of Statement 19, wherein the core sample is fluidly isolated from the vessel fluid and one or more external fluid supplies are coupled to the overburden stress apparatus to perform the production test or the injection test on the core sample.

I claim:

1. An overburden stress apparatus comprising:
   an elongate fixture shell enclosing and isolating a chamber;
   a plurality of stress members within the chamber and arranged to form a rectangular prism shaped central receiving cavity for containing a core sample of rock to be tested, the plurality of stress members covering at least five faces of the rectangular shaped receiving cavity, the rectangular prism shaped receiving cavity having three opposite paired faces and having three axes extending one through each of the three opposite paired faces, the plurality of stress members independently controllable to apply overburden pressures to the core sample when the core sample is contained within the central receiving cavity in the direction of each of the three axes;
   a first end adapter positioned at a first end of the central receiving cavity for receiving a first end of the core sample when contained therein, wherein the first end adapter comprises:
      a perforation port configured to receive a perforator or perforating gun during a perforation test on the core sample; and
      a casing receptacle configured to receive a simulated casing and cement coupon to abut the core sample; and
   a second end adapter positioned at a second end of the central receiving cavity opposite the first end, and covering at least one of the plurality of stress members;
   wherein the fixture shell is configured to receive an external pressure from an external pressure vessel, the fixture shell configured to support only a portion of the overburden pressures and the external pressure supports a remaining portion of the overburden pressures.

2. The overburden stress apparatus of claim 1, further comprising an external pressure vessel, the fixture shell being contained within the external pressure vessel and receiving an external pressure from the external pressure vessel, the fixture shell configured to support only a portion of the overburden pressures, the external pressure supporting a remaining portion of the overburden pressures.

3. The overburden stress apparatus of claim 1, wherein the plurality of stress members are independently controllable to generate three overburden stress profiles along the corresponding three axes.

4. The overburden stress apparatus of claim 1, wherein the plurality of stress members are provided by one or more of flat jacks and pistons.

5. The overburden stress apparatus of claim 1, wherein the core sample is rectangular in cross-section and less than 12 inches on a side in cross-section.

6. The overburden stress apparatus of claim 1, further comprising a simulated wellbore section, the simulated wellbore section coupled between the first end adapter and a pressurized fluid source for simulating wellbore characteristics.

7. The overburden stress apparatus of claim 1, wherein the first end of the core sample is received into a simulated wellbore casing portion of the first end adapter.

8. The overburden stress apparatus of claim 1, wherein the second end adapter provides a fluid coupling between a pressurized source of pore fluid and the core sample.

9. The overburden stress apparatus of claim 1, further comprising a perforator coupled to a simulated wellbore casing portion of the first end adapter, the perforator operable to create a perforation tunnel through the simulated wellbore casing portion and into the core sample.

10. A method, comprising:
    positioning a core sample of rock within a fixture shell of an overburden stress apparatus, the overburden stress apparatus comprising:
       a plurality of stress members within a chamber and arranged to form a rectangular prism shaped central receiving cavity for containing the core sample of rock to be tested, the plurality of stress members covering at least five faces of the rectangular shaped receiving cavity, the rectangular prism shaped receiving cavity having three opposite paired faces and having three axes extending one through each of the three opposite paired faces, the plurality of stress members independently controllable to apply overburden pressures to the core sample when the core sample is contained within the central receiving cavity in the direction of each of the three axes; and
       a first end adapter positioned at a first end of the central receiving cavity for receiving a first end of the core sample when contained therein, wherein the first end adapter comprises:
          a perforation port configured to receive a perforator or perforating gun during a perforation test on the core sample; and
          a casing receptacle for receiving a simulated casing and cement coupon to abut the core sample; and
       a second end adapter positioned at a second end of the central receiving cavity opposite the first end, and covering at least one of the plurality of stress members;
    positioning the overburden stress apparatus within the interior volume of an external pressure vessel containing a vessel fluid;
    pressurizing the external pressure vessel to a desired vessel pressure, such that the vessel pressure provides circumferential support to the fixture shell; and
    pressurizing the overburden stress apparatus to desired triaxial overburden pressures along a first axis, a second axis, and a third axis of the core sample, wherein the fixture shell supports only a portion of the overburden pressures and the vessel pressure supports the remaining portion of the overburden pressures.

11. The method of claim 10, wherein a maximum rated pressure of the fixture shell is less than one or more of the vessel pressure and the triaxial overburden pressures.

12. The method of claim 10, further comprising adjusting the triaxial overburden pressures to generate a desired first overburden stress profile along the first axis of the core sample, a desired second overburden stress profile along the second axis of the core sample, and a desired third overburden stress profile along the third axis of the core sample.

13. The method of claim 10, wherein the external pressure vessel and the overburden stress apparatus are pressurized simultaneously, such that a differential between the vessel pressure and any of the triaxial overburden pressures never exceeds a threshold pressure, wherein the threshold pressure is a function of a maximum rated pressure of the fixture shell.

14. The method of claim 10, wherein the external pressure vessel and the overburden stress apparatus are step-wise pressurized, wherein the vessel pressure and the triaxial overburden pressures are raised in alternating fashion by an amount less than the desired vessel pressure and the desired triaxial overburden pressures, respectively.

15. The method of claim 10, wherein pressurizing the overburden stress apparatus comprises adjusting a plurality of stress members positioned in the interior of the fixture shell and in contact with the core sample, the stress members provided by one or more of flat jacks and pistons.

16. The method of claim 10, further comprising providing a simulated wellbore casing portion between a face of the core sample and the external pressure vessel.

17. The method of claim 16, further comprising performing a perforation test on the core sample, the perforation test creating a perforation tunnel through the simulated wellbore casing portion and extending into the core sample.

18. The method of claim 16, wherein a perforation tunnel is used to perform a production test or an injection test on the core sample.

19. The method of claim 18, wherein the core sample is fluidly isolated from the vessel fluid and one or more external fluid supplies are coupled to the overburden stress apparatus to perform the production test or the injection test on the core sample.

* * * * *